(12) United States Patent
Hawkins

(10) Patent No.: US 6,589,778 B1
(45) Date of Patent: Jul. 8, 2003

(54) METHOD AND APPARATUS FOR PERFORMING BIOLOGICAL REACTIONS ON A SUBSTRATE SURFACE

(75) Inventor: George W. Hawkins, Gilbert, AZ (US)

(73) Assignee: Amersham Biosciences AB (SE)

( * ) Notice: Subject to any disclaimer, the term of this patent is extended or adjusted under 35 U.S.C. 154(b) by 0 days.

(21) Appl. No.: 09/464,490

(22) Filed: Dec. 15, 1999

(51) Int. Cl.$^7$ .............................. C12M 1/34; C12Q 1/68; C12P 19/34; C07H 21/02; C07H 21/04

(52) U.S. Cl. .................. 435/287.2; 435/6; 435/7.1; 435/91.1; 435/91.2; 536/22.1; 536/23.1; 536/24.3; 536/24.31; 536/24.32; 536/24.33

(58) Field of Search .................. 435/6, 91.1, 91.2; 536/287.2, 22.1, 23.1, 24.3, 24–31, 24.32, 24.33

(56) References Cited

U.S. PATENT DOCUMENTS

| | | | |
|---|---|---|---|
| 4,908,319 A | | 3/1990 | Smyczek et al. |
| 5,038,852 A | | 8/1991 | Johnson et al. |
| 5,100,775 A | | 3/1992 | Smyczek et al. |
| 5,143,854 A | | 9/1992 | Pirrung et al. |
| 5,169,697 A | * | 12/1992 | Langley ..................... 428/57 |
| 5,360,741 A | | 11/1994 | Hunnell |
| 5,474,796 A | | 12/1995 | Brennan |
| 5,492,806 A | | 2/1996 | Drmanac et al. |
| 5,525,464 A | | 6/1996 | Drmanac et al. |
| 5,541,061 A | | 7/1996 | Fodor et al. |
| 5,545,531 A | | 8/1996 | Rava et al. |
| 5,571,639 A | | 11/1996 | Hubbell et al. |
| 5,578,832 A | | 11/1996 | Trulson et al. |
| 5,580,717 A | | 12/1996 | Dower et al. |
| 5,593,839 A | | 1/1997 | Hubbell et al. |
| 5,599,695 A | | 2/1997 | Pease et al. |
| 5,631,734 A | | 5/1997 | Stern et al. |
| 5,695,940 A | | 12/1997 | Drmanac et al. |
| 5,733,729 A | | 3/1998 | Lipshutz et al. |
| 5,744,305 A | | 4/1998 | Fodor et al. |
| 5,770,456 A | | 6/1998 | Holmes |
| 5,786,439 A | * | 7/1998 | Van Antwerp et al. ....... 528/77 |
| 5,834,758 A | | 11/1998 | Trulson et al. |
| 5,837,832 A | | 11/1998 | Chee et al. |
| 5,843,655 A | | 12/1998 | McGall |
| 5,847,105 A | | 12/1998 | Baldeschwieler et al. |
| 5,856,101 A | | 1/1999 | Hubbell et al. |
| 5,856,174 A | | 1/1999 | Lipshutz et al. |
| 5,861,242 A | | 1/1999 | Chee et al. |
| 5,874,219 A | | 2/1999 | Rava et al. |
| 5,882,930 A | | 3/1999 | Baier |
| 5,905,024 A | * | 5/1999 | Mirzabekov et al. .......... 435/6 |
| 5,922,591 A | | 7/1999 | Anderson et al. |
| 5,945,334 A | | 8/1999 | Besemer et al. |
| 5,955,283 A | | 9/1999 | Bandman et al. |
| 5,955,284 A | | 9/1999 | Braxton et al. |
| 5,960,014 A | * | 9/1999 | Li et al. ..................... 372/20 |
| 6,109,113 A | * | 8/2000 | Chavan et al. ............... 73/718 |
| 6,171,793 B1 | * | 1/2001 | Phillips et al. ................. 435/6 |
| 6,372,813 B1 | * | 4/2002 | Johnson et al. ............. 522/114 |

FOREIGN PATENT DOCUMENTS

| | | |
|---|---|---|
| WO | WO 91/07087 | 5/1991 |
| WO | WO 97/10056 A2 | 3/1997 |
| WO | WO 99/19717 A1 | 4/1999 |
| WO | WO 99/42558 A1 | 8/1999 |

OTHER PUBLICATIONS

Rehman et al., "Immobilization of acrylamide–modified oligonucleotides by co–polumerization," Nucleic Acids Research, 27(2): 649–655 (1999).

* cited by examiner

*Primary Examiner*—Jeffrey Siew
(74) *Attorney, Agent, or Firm*—Robin M. Silva; Dorsey & Whitney LLP

(57) ABSTRACT

The present invention provides an apparatus for performing biological reactions on a substrate layer having a multiplicity of oligonucleotide binding sites disposed thereon. The invention provides a hybridization chamber wherein nucleic acid hybridization is performed by reacting biological material on a biochip comprising a substrate having an array of oligonucleotide binding sites. The binding sites are associated with an array of 3-dimensional polyacrylamide pads for anchoring the reactants. The arrays are covered with a flexible layer that permits mixing of the hybridization solution on the biochip and detection of hybridization in situ. Fluid inlet and outlet ports in the chamber provide for control of fluid flow into and out of the chamber.

23 Claims, 10 Drawing Sheets

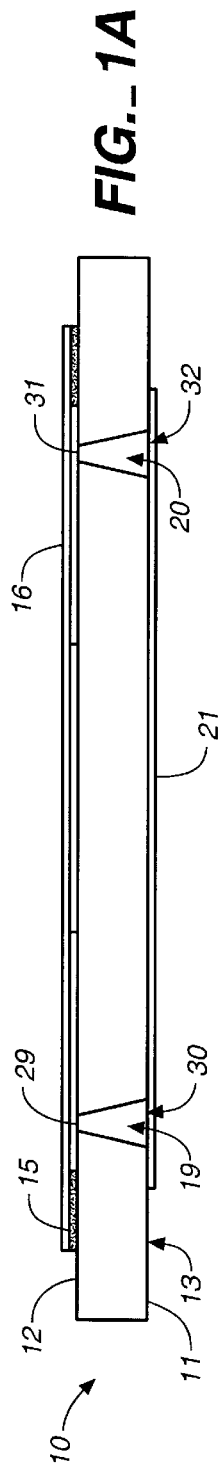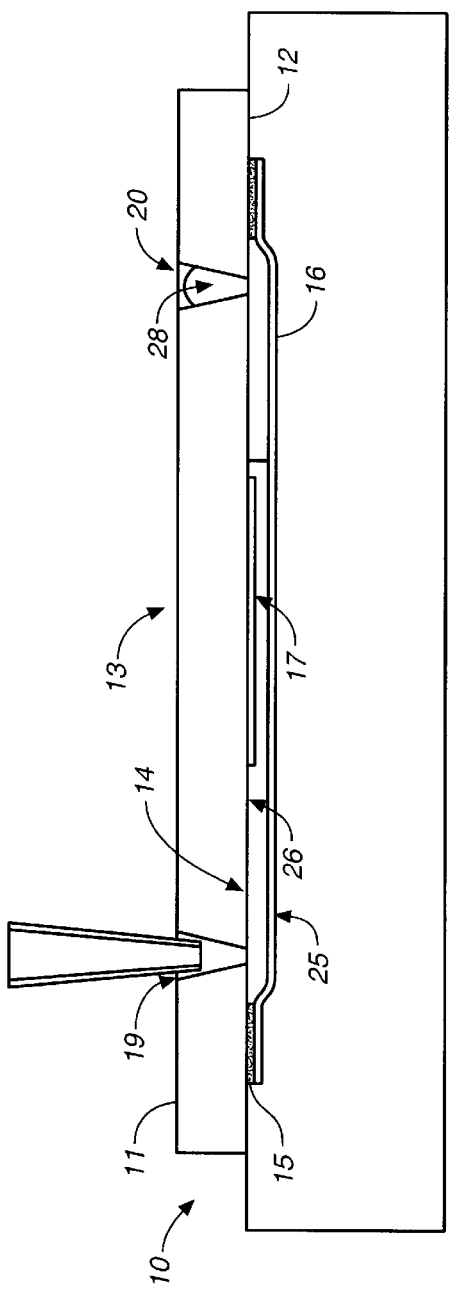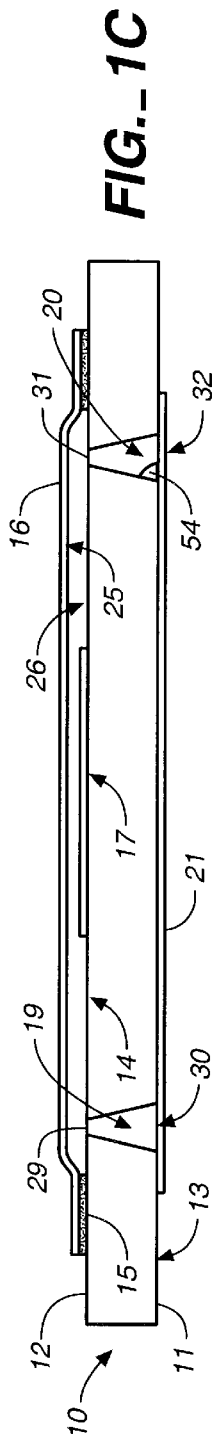

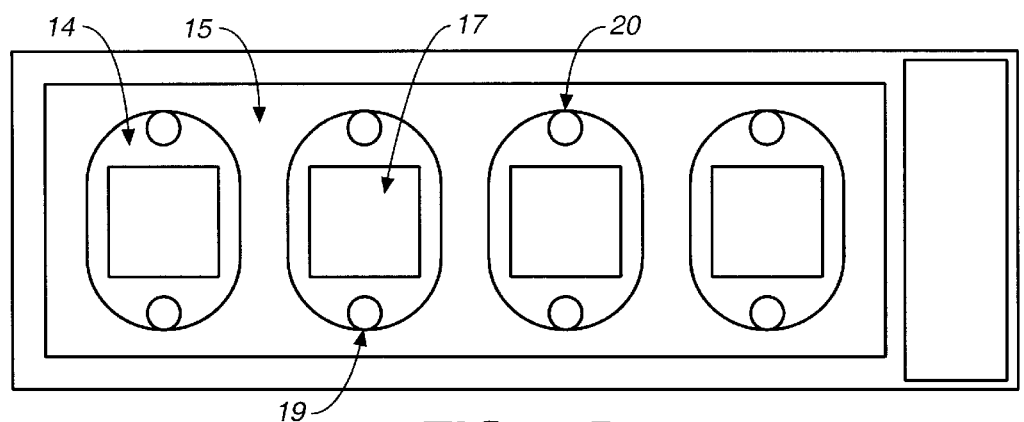
FIG._1D
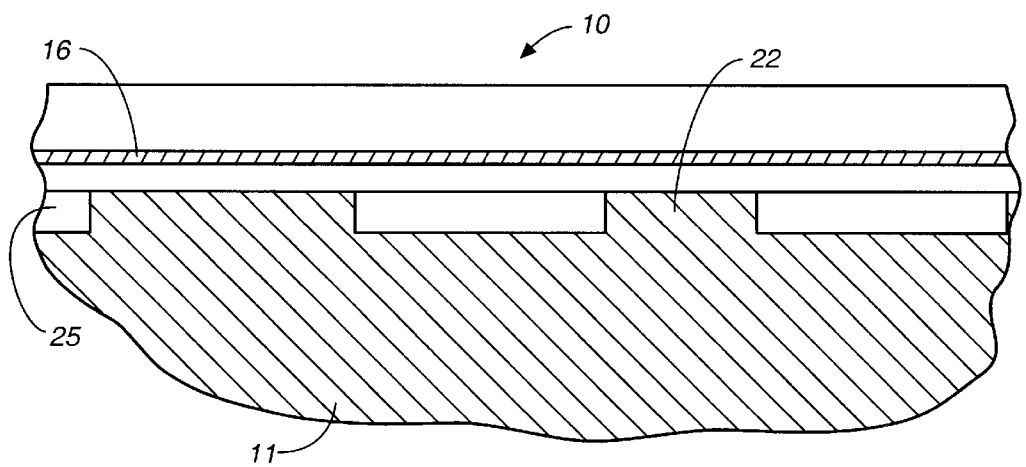
FIG._2

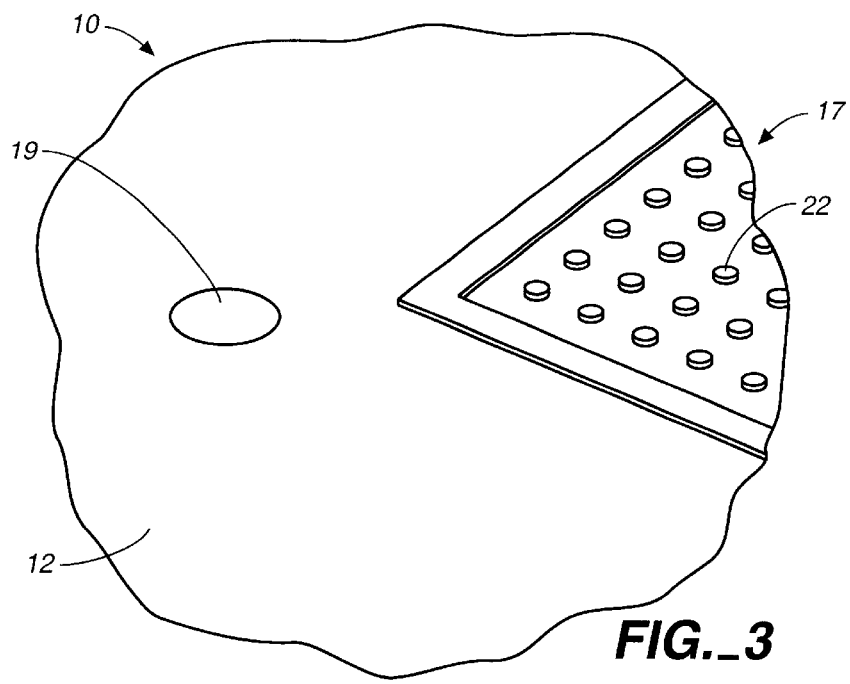
FIG._3
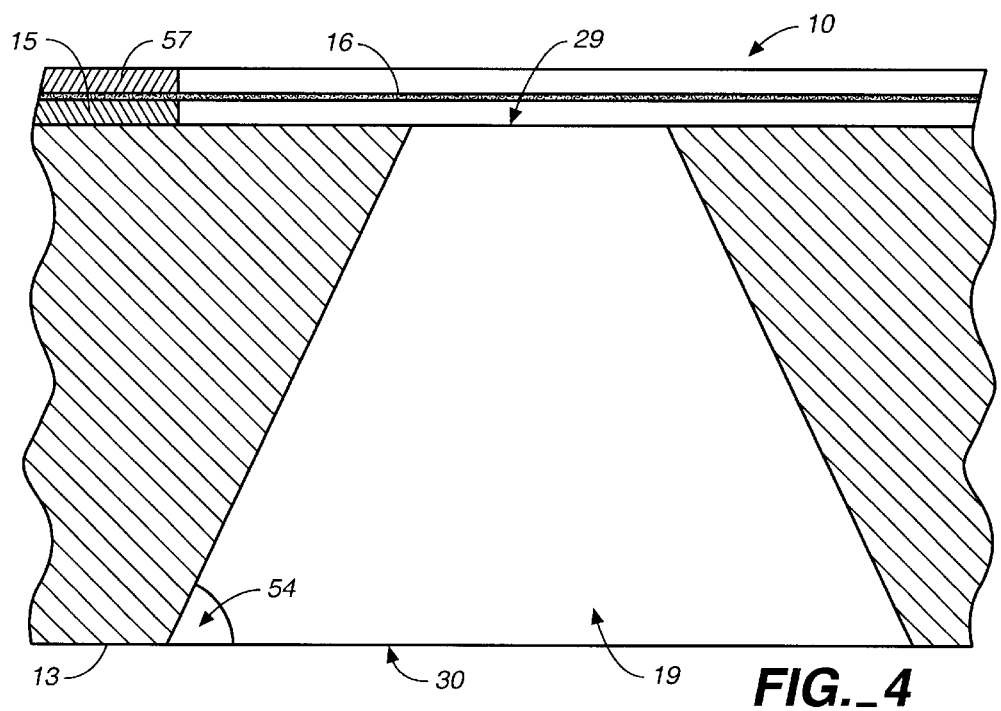
FIG._4

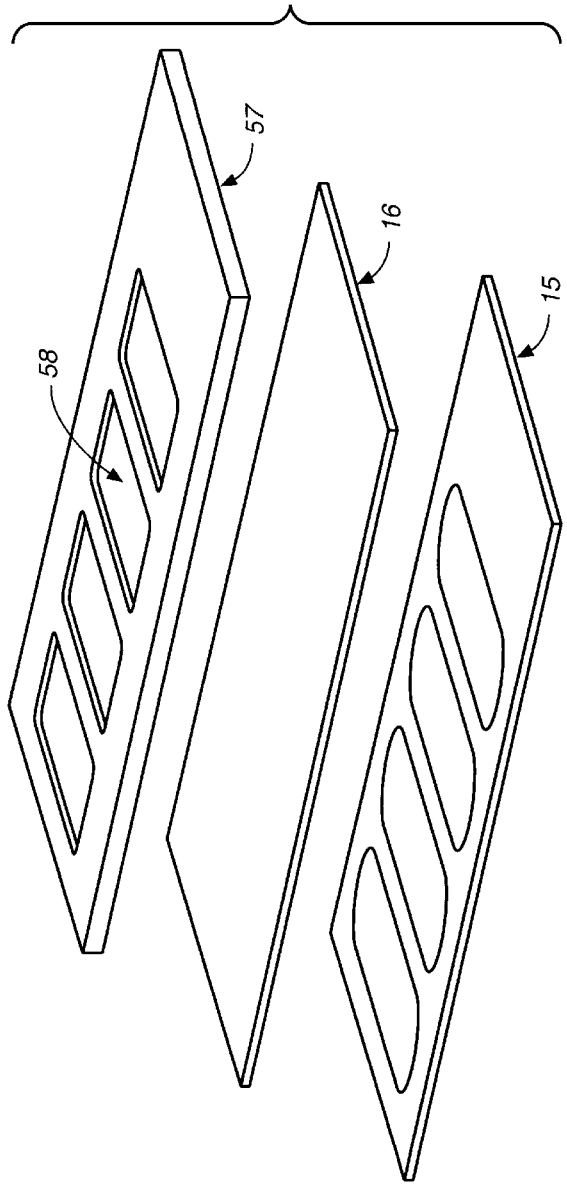
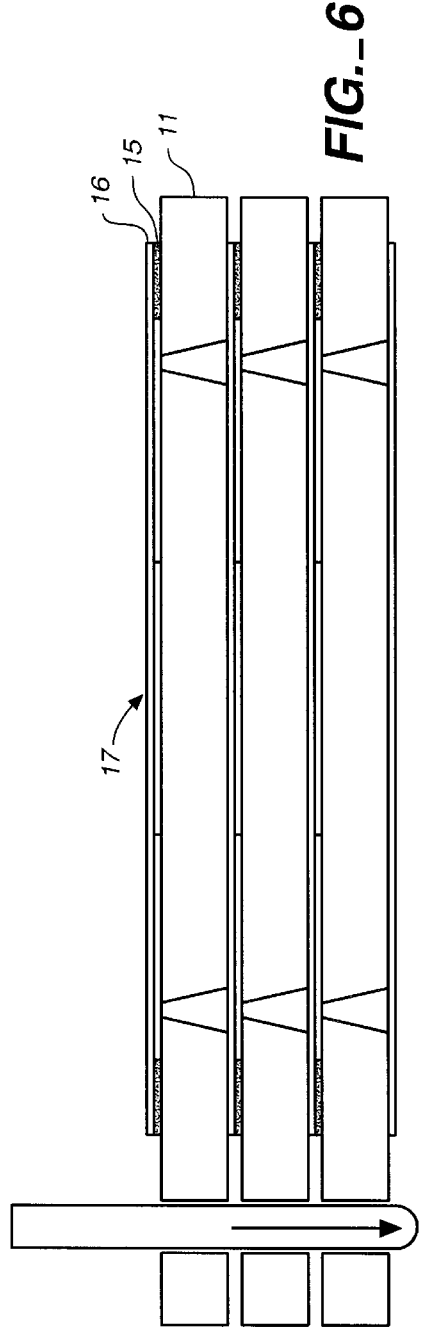

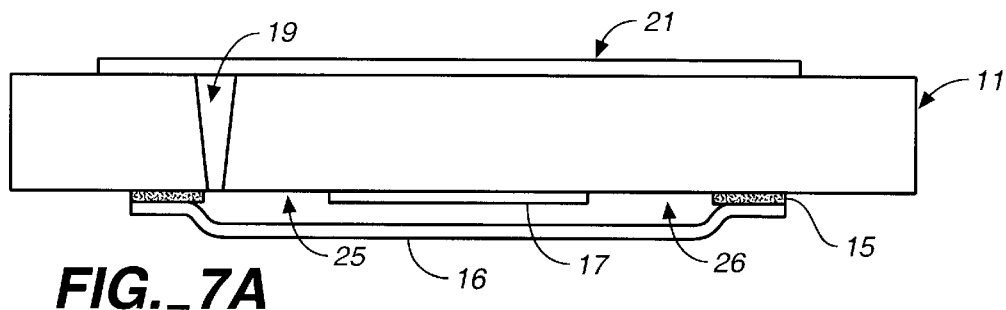
FIG._7A
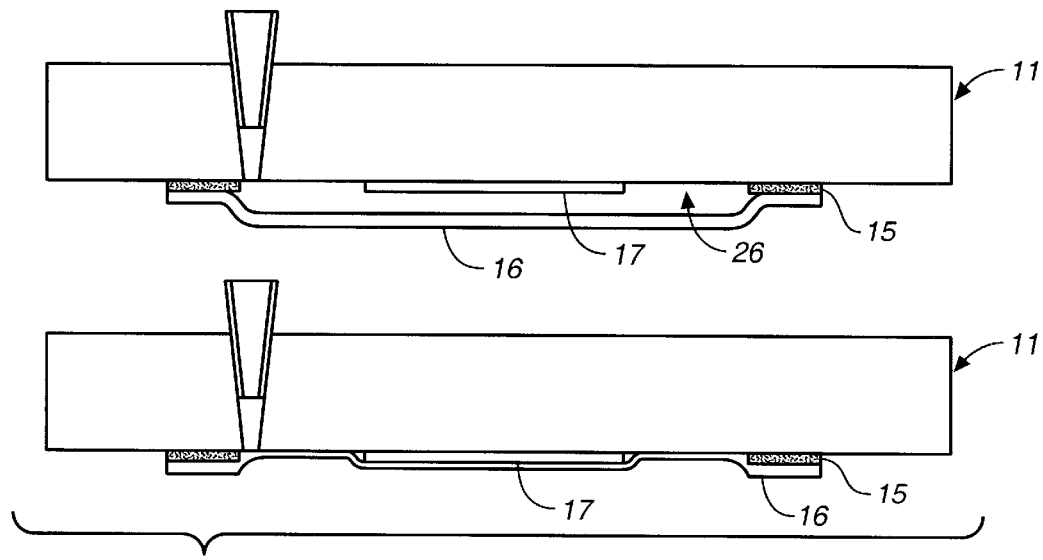
FIG._7B
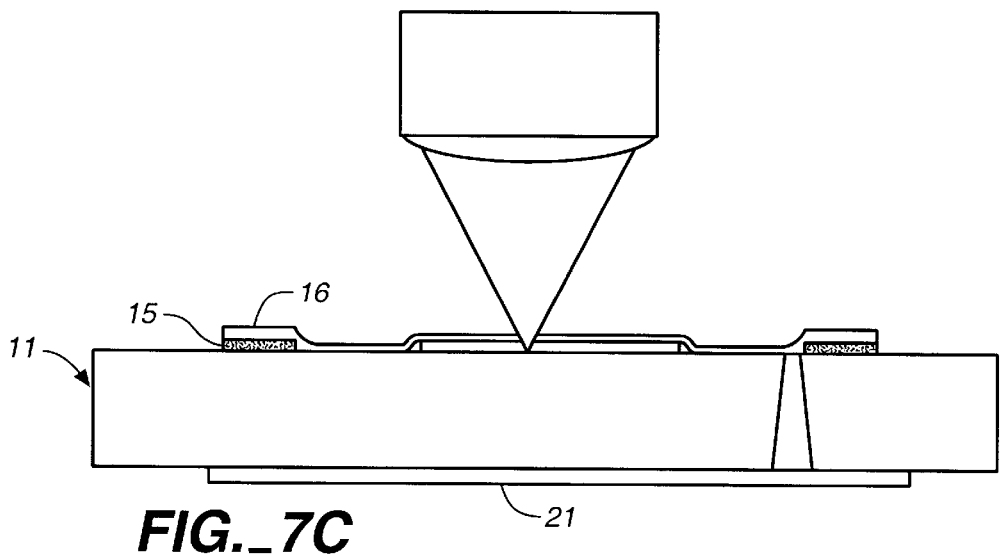
FIG._7C

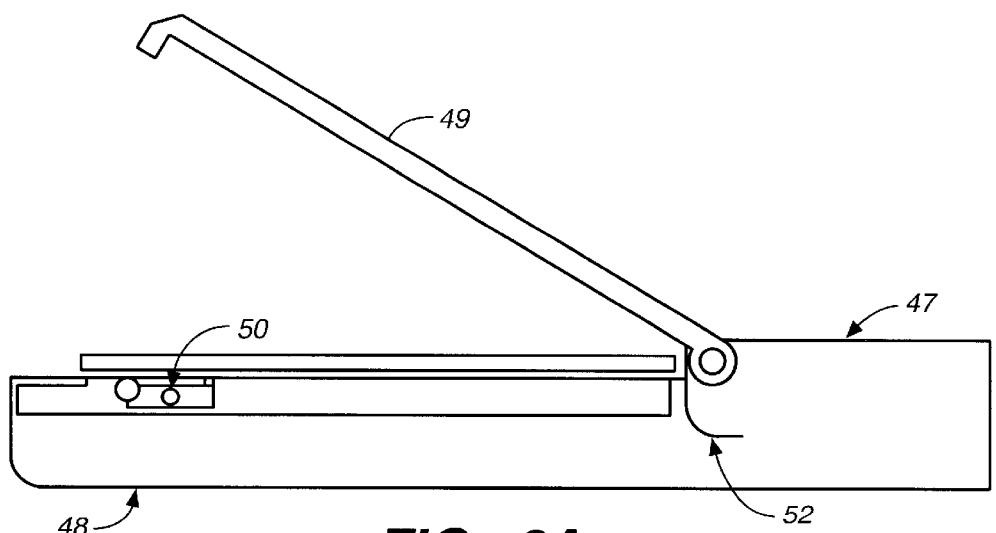
FIG._8A
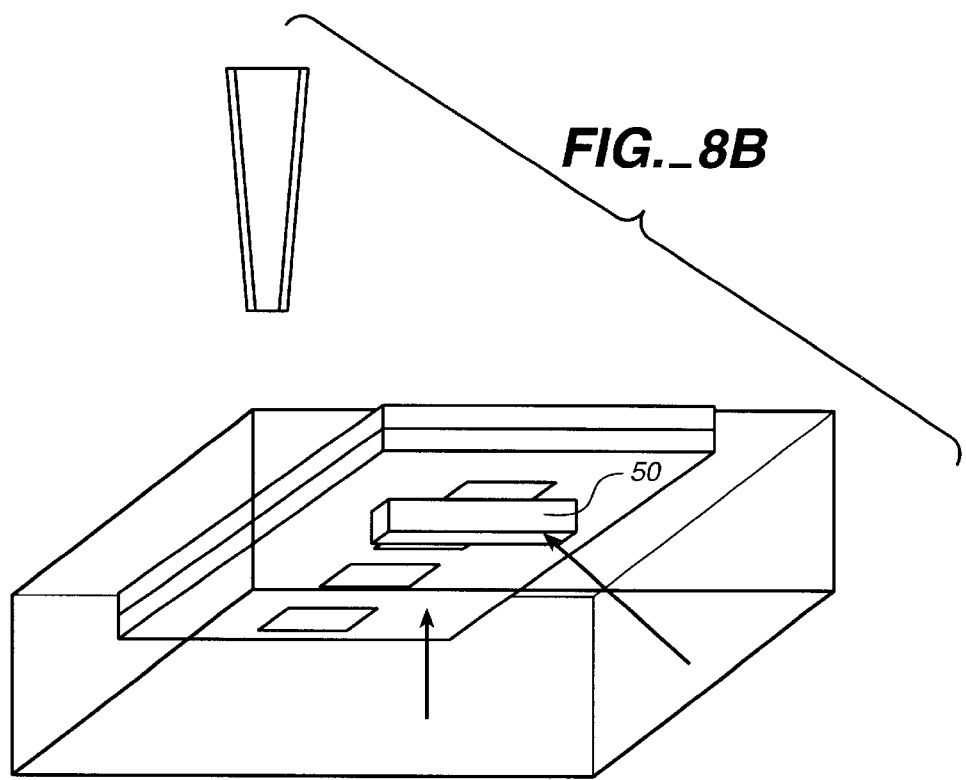
FIG._8B

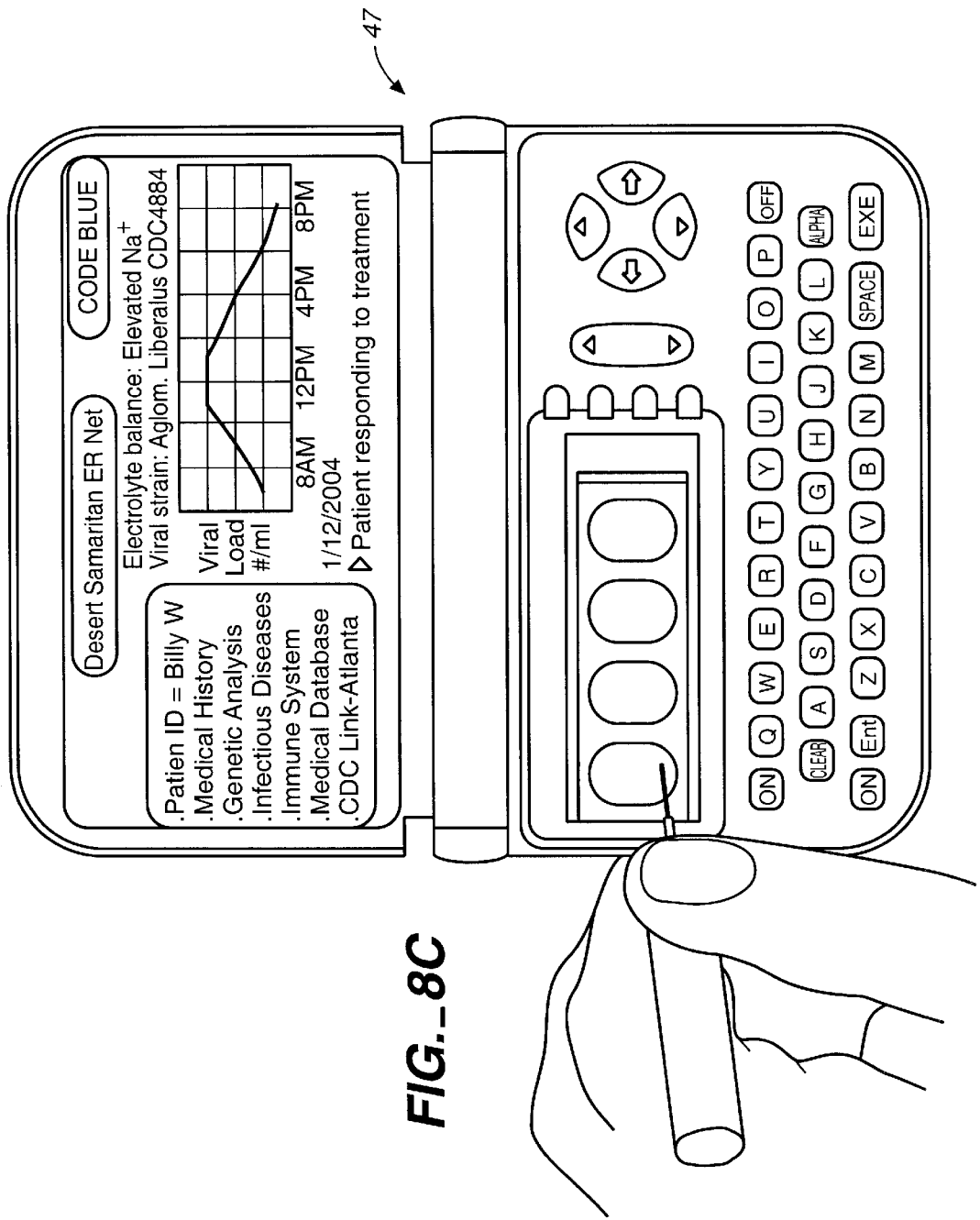
FIG._8C

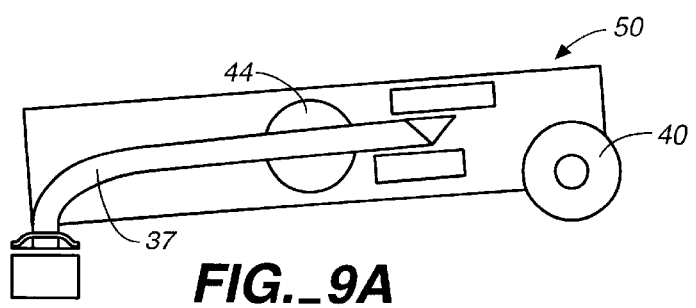
FIG._9A
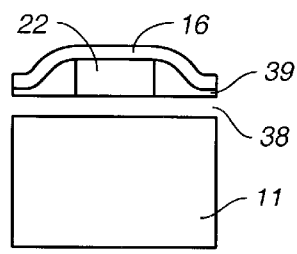
FIG._9C
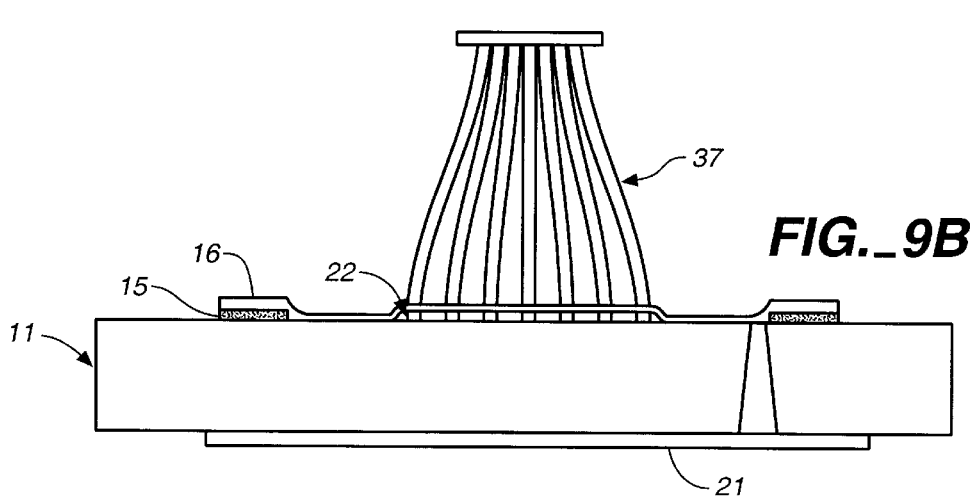
FIG._9B
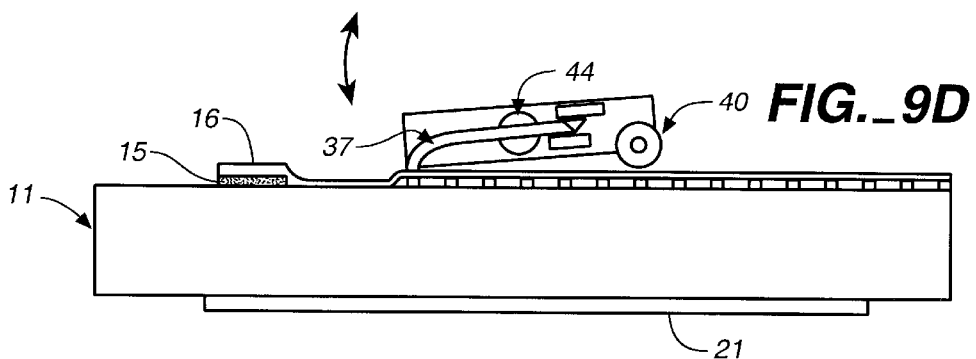
FIG._9D
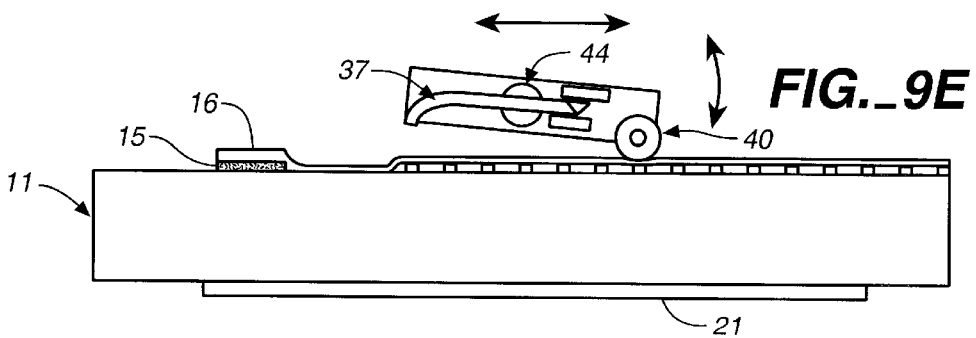
FIG._9E

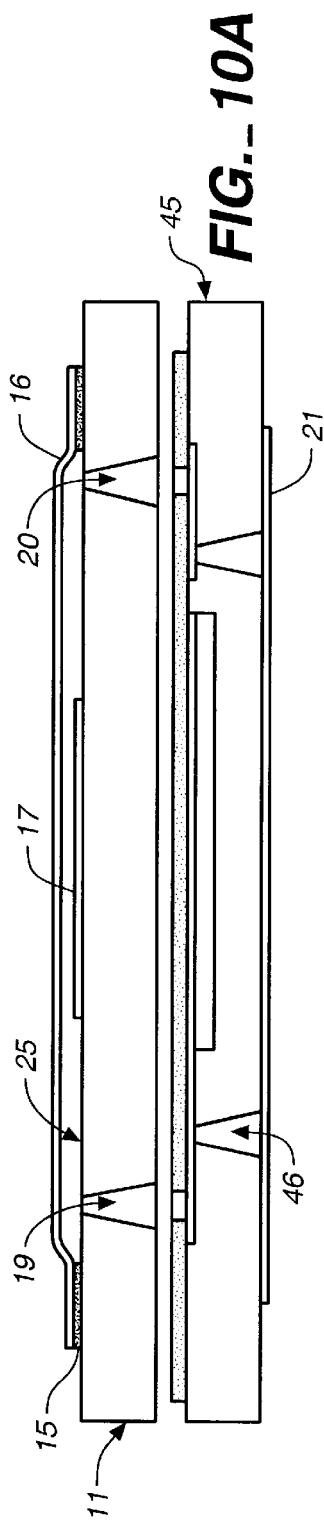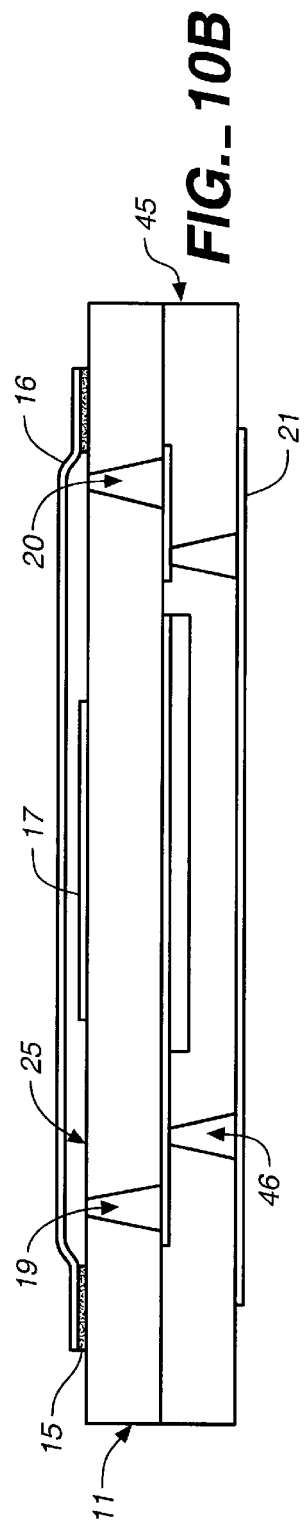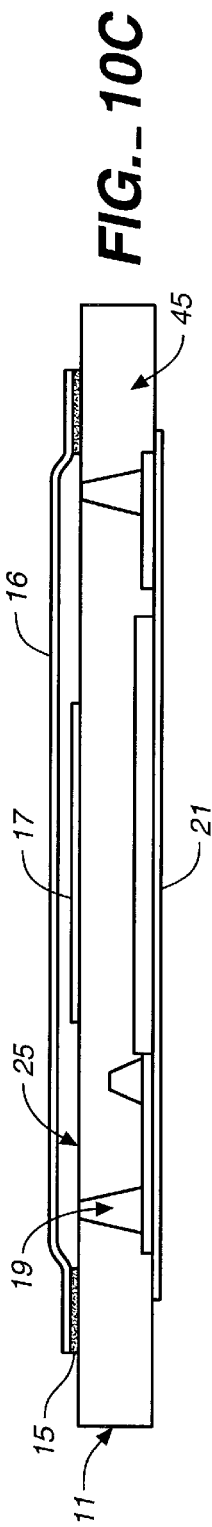

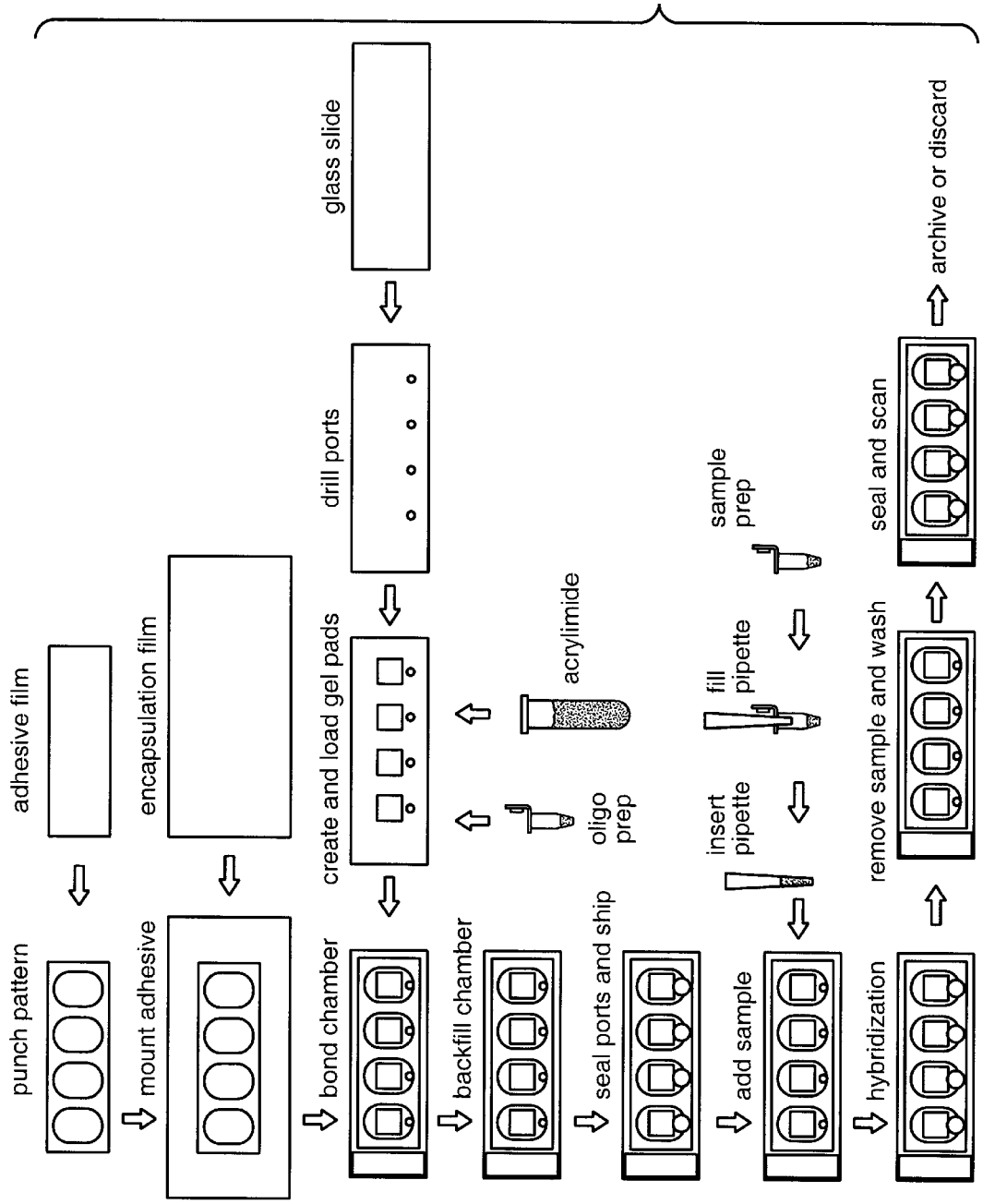
FIG._11

METHOD AND APPARATUS FOR PERFORMING BIOLOGICAL REACTIONS ON A SUBSTRATE SURFACE

BACKGROUND OF THE INVENTION

1. Field of the Invention

The present invention relates to an apparatus for performing biological reactions. Specifically, the invention relates to an apparatus for performing nucleic acid hybridization reactions on a substrate layer having a multiplicity of oligonucleotide binding sites disposed thereon.

2. Description of the Prior Art

Recent advances in molecular biology have provided the opportunity to identify pathogens, diagnose disease states, and perform forensic determinations using gene sequences specific for the desired purpose. This explosion of genetic information has created a need for high-capacity assays and equipment for performing molecular biological assays, particularly nucleic acid hybridization assays. Most urgently, there is a need to miniaturize, automate, standardize and simplify such assays. This need stems from the fact that while these hybridization assays were originally developed in research laboratories working with purified products and performed by highly skilled individuals, adapting these procedures to clinical uses, such as diagnostics, forensics and other applications, has produced the need for equipment and methods that allow less-skilled operators to effectively perform the assays under higher capacity, less stringent assay conditions.

Nucleic acid hybridization assays are advantageously performed using probe array technology, which utilizes binding of target single-stranded DNA onto immobilized DNA (usually, oligonucleotide) probes. The detection limit of a nucleic acid hybridization assay is determined by the sensitivity of the detection device, and also by the amount of target nucleic acid available to be bound to probes, typically oligonucleotide probes, during hybridization.

Nucleic acid hybridization chambers are known in the prior art.

U.S. Pat. No. 5,100,755 to Smyczek et al. discloses a hybridization chamber.

U.S. Pat. No. 5,545,531 to Rava et al. discloses a hybridization plate comprising a multiplicity of oligonucleotide arrays.

U.S. Pat. No. 5,360,741 to Hunnell discloses a gas heated hybridization chamber.

U.S. Pat. No. 5,922,591 to Anderson et al. discloses a miniaturized hybridization chamber for use with oligonucleotide arrays.

U.S. Pat. No. 5,945,334 to Besemer discloses oligonucleotide array packaging.

As currently employed, oligonucleotide array technology does not provide maximum hybridization efficiency. Existing nucleic acid hybridization assay equipment includes numerous components, each of which is a source of inefficiency and inaccuracy.

Hybridization using oligonucleotide arrays must be performed in a volume in which a small amount of target DNA or other nucleic acid can be efficiently annealed to the immobilized probes. For diagnostic assays, target DNA molecules are often obtained in minute (<picomol) quantities. In practice, it can take several (tens of) hours for hybridization to be substantially complete at the low target nucleic acid levels available for biological samples.

In addition, array hybridization is conventionally performed in a stationary hybridization chamber where active mixing is absent. Under these conditions, the probability that a particular target molecule will hybridize to a complementary oligonucleotide probe immobilized on a surface is determined by the concentration of the target, the diffusion rate of the target molecule and the statistics of interaction between the target and the complementary oligonucleotide.

Consequently, a larger number of samples must be tested to obtain useful information, and this in turn leads to increased hybridization times and inefficiencies.

In addition, efficiency is increased when the amount of user manipulation is kept to a minimum. As currently performed, oligonucleotide array hybridization requires a great deal of operator attentiveness and manipulation, and the degree of skill required to perform the analysis is high. For example, hybridization is typically performed in an assay chamber, and then data collection and analysis are performed in a separate apparatus (such as a laser scanner or fluorescence microscope). This arrangement requires a substantial amount of handling by the user, and makes the assays both time-consuming and subject to user error.

It is also a limitation of current practice that array hybridizations are performed one array at a time, thereby forgoing the economies of parallel processing and data analysis.

Additional limitations, inefficiencies, and expenses arise from the structural characteristics of existing apparatus. Many existing apparatus are limited in the size of the substrate they can accommodate. Other apparatus are not disposable and therefore require extensive cleaning between runs in order to prevent sample contamination. Yet other apparatus are high mass and therefore not susceptible of the rapid heating and cooling necessary for efficient hybridization. Other apparatus require the use of expensive optics for analysis of the reaction products.

There remains a need in this art for an easy-to-use apparatus for performing biological reactions, particularly nucleic acid hybridization, that comprises a small reaction volume, where the fluid components can be actively mixed, that can be performed in parallel and that minimizes user intervention. There also remains a need for such an apparatus that is easy to manufacture in various sizes, that is disposable to minimize sample contamination, that allows for the use of low cost optical analytical equipment, and that is low mass to allow for rapid heating and cooling of the sample fluid. There also remains a need for methods for using such apparatus to increase hybridization efficiency, particularly relating to biochip arrays as understood in the art. This need is particularly striking, in view of the tremendous interest in biochip technology, the investment and substantial financial rewards generated by research into biochip technology, and the variety of products generated by such research.

SUMMARY OF THE INVENTION

The invention provides an apparatus in which biological reactions such as nucleic acid hybridization can be performed. The apparatus of the invention is a hybridization chamber comprising a flexible layer attached to a biochip by an adhesive layer. The biochip comprises a substrate having a first surface and a second surface, wherein the first surface contains an array of biologically reactive sites, preferably an oligonucleotide array. The array is provided in an area bounded by the adhesive layer set down on the first substrate surface. The flexible layer most preferably is both deformable and translucent. The chamber also includes a first port, and certain embodiments further include a second port, that transverses the substrate and comprises a first opening on the first substrate surface and a second opening on the second substrate surface. The openings of these ports on the second substrate surface are covered by a removable cover, most preferably a foil tape. The openings of these ports on the first substrate surface are provided within the area bounded by the adhesive layer. The adhesive layer, the flexible layer and the substrate also define a volume that is filled with a water-soluble compound. The water-soluble compound is preferably a solid at certain temperatures, most preferably at or below room temperature, and a liquid at elevated temperatures, most preferably below about 100° C.

In certain embodiments of the invention, the substrate comprises a multiplicity of oligonucleotide arrays, which are contained in one or a plurality of areas bounded by the adhesive layer and covered by the flexible layer. In these embodiments, each area bounded by the adhesive layer also comprises a first port and can also comprise a second port.

The hybridization chamber is optionally supplied with a heater, most preferably a resistive heater, in thermal contact with the flexible layer. The chamber is also optionally supplied with a roller, most preferably a patterned roller, positioned in contact with the flexible layer and movable longitudinally across the surface of the chamber for mixing hybridization fluid and wash solutions as required. The chamber is further optionally supplied with a scanner positioned in contact with the flexible layer and movable longitudinally across the surface of the chamber for detecting hybridization signals, most preferably produced by fluorescently-labeled target nucleic acid.

In a further preferred embodiment, the invention provides a handheld device comprising a lid, a base, a carriage embodying a roller, a scanner, a heating element and a thermocouple, wherein the hybridization chamber of the invention is positioned above and in removable contact with the carriage.

Specific preferred embodiments of the present invention will become evident from the following more detailed description of certain preferred embodiments and the claims.

DESCRIPTION OF THE DRAWINGS

Presently preferred embodiments of the invention are described with reference to the following drawings.

FIGS. 1A–1D are views of a preferred embodiment of the present invention illustrating the preparation of a chamber for reaction. FIG. 1A is a cross-sectional view of the apparatus illustrating a hybridization chamber prefilled with a water-soluble compound in thermal contact with a heating element. FIG. 1B is a cross sectional view of the apparatus illustrating the mixing of the water-soluble compound and the biological sample fluid. FIG. 1C is a cross sectional view of the apparatus illustrating a chamber filled with the sample fluid/water-soluble compound mixture, wherein the first and second ports are covered with a seal. FIG. 1D is a top plan view of the apparatus illustrating the pattern of adhesive defining the individual areas containing the arrays of oligonucleotide probes.

FIG. 2 is an exploded cross-sectional view of a chamber showing the array of gel pads of a preferred embodiment of the invention.

FIG. 3 is an exploded perspective view of the array of biomolecular probes showing the positioning of the gel pads on the substrate of a preferred embodiment of the invention.

FIG. 4 is an exploded cross-sectional view of a port illustrating the conical shape of the port of a preferred embodiment of the invention.

FIG. 5 is a perspective view of the label layer, the flexible layer and the adhesive layer of a preferred embodiment of the invention.

FIG. 6 is a cross-sectional view of a stack of chambers according to a preferred embodiment.

FIGS. 7A–7C are cross-sectional views of a preferred embodiment of the present invention illustrating the process of analyzing the array after completion of the reaction. FIG. 2A shows the apparatus upon completion of the reaction. FIG. 2B illustrates removal of the sample fluid from the chamber such that the flexible layer contacts the array. FIG. 2C illustrates use of a laser scanner to analyze the array.

FIGS. 8A–8C illustrate a handheld embodiment of the present invention. FIG. 8A is a side view of the hand held scanning system. FIG. 8B is a perspective view of a preferred embodiment comprising a hand-held scanning device illustrating the contact of the flexible layer with the carriage. FIG. 8C is a view of the handheld system illustrating the lid containing the display unit.

FIGS. 9A–9E are cross-sectional views of the direct contact fiber optic scanner as shown in FIG. 8.

FIGS. 10A–10C are alternate embodiments illustrating the apparatus coupled to a sample preparation chip. FIG. 10A illustrates an embodiment wherein the sample preparation chip is removably positioned against the second surface of the substrate. FIG. 10B illustrates an embodiment wherein the sample preparation chip is affixed to the second surface of the substrate. FIG. 10C illustrates an embodiment wherein the sample preparation chip is incorporated into the substrate.

FIG. 11 illustrates the assembly and use of a preferred embodiment of the present invention.

DETAILED DESCRIPTION OF THE PREFERRED EMBODIMENTS

The present invention provides an apparatus for performing high-capacity biological reactions on a biochip comprising a substrate having an array of biological binding sites. The invention provides a hybridization chamber having one or more arrays, preferably comprising arrays consisting of gel pads and most preferably comprising arrays consisting of 3-dimensional polyacrylamide gel pads, wherein nucleic acid hybridization is performed by reacting a biological sample containing a target molecule of interest with a complementary oligonucleotide probe immobilized on the biochip. In preferred embodiments, the array is an oligonucleotide array comprising at least about 400, more preferably at least about 1000 and most preferably at least about 10,000 oligonucleotide probes. In these embodiments, the apparatus is most preferably used for nucleic acid hybridization of target nucleic acids in a biological sample, wherein the biological samples include, but are not limited to, nucleic acids, including DNA, genomic DNA, cDNA, and RNA.

As used herein, the term "array" refers to an ordered spatial arrangement, particularly an arrangement of immobilized biomolecules or polymeric anchoring structures.

As used herein, the term "addressable array" refers to an array wherein the individual elements have precisely defined x and y coordinates, so that a given element can be pinpointed.

As used herein, the term "biomolecular probe" refers to a biomolecule used to detect a complementary biomolecule. Examples include antigens which detect antibodies, oligonucleotides which detect complimentary oligonucleotides, and ligands which detect receptors. Such probes are preferably immobilized on a substrate.

As used herein, the term "oligonucleotide probe" refer to a nucleic acid sequence used to detect the presence of a complementary target sequence by hybridization with the target sequence.

As used herein, the term "biochip" refers to an array of biomolecular probes, preferably oligonucleotide probes, immobilized on a substrate.

The invention is advantageously used for performing assays using biochips 18. Biochips, as used in the art, encompass substrates containing arrays or microarrays, preferably ordered arrays and most preferably ordered, addressable arrays, of biological molecules that comprise one member of a biological binding pair. Typically, such arrays are oligonucleotide arrays comprising a nucleotide sequence that is complementary to at least one sequence expected to be present in a biological sample. Alternatively, peptides or other small molecules can be arrayed in such biochips for performing immunological analysis (wherein the arrayed molecules are antigens) or assaying biological receptors (wherein the arrayed molecules are ligands, agonists or antagonists of said receptors).

One key feature of biochips is the manner in which the arrayed biomolecules are attached to the surface of the biochip. Conventionally such procedures involve multiple reaction steps, often requiring chemical modification of the solid support itself. Even in embodiments comprising absorption matrices, such as hydrogels, present on a solid support, chemical modification of the gel polymer is necessary to provide a chemical functionality capable forming a covalent bond with the biomolecule. The efficiency of the attachment chemistry and strength of the chemical bonds formed are critical to the fabrication and ultimate performance of the micro array.

Polyacrylamide hydrogels and gel pads are used as binding layers to adhere to surfaces biological molecules including, but not limited to, proteins, peptides, oligonucleotides, polynucleotides, and larger nucleic acid fragments. The gel pads comprising biochips for use with the apparatus of the present invention are conveniently produced as thin sheets or slabs, typically by depositing a solution of acrylamide monomer, a crosslinker such methylene bisacrylamide, and a catalyst such as N,N,N',N'-tetramethylethylendiamine (TEMED) and an initiator such as ammonium persulfate for chemical polymerization, or 2,2-dimethoxy-2-phenyl-acetophone (DMPAP) for photopolymerization, in between two glass surfaces (e.g., glass plates or microscope slides) using a spacer to obtain the desired thickness of polyacrylamide gel. Generally, the acrylamide monomer and crosslinker are prepared in one solution of about 4–5% acrylamide (having an acrylamide/bisacrylamide ratio of 19/1) in water/glycerol, with a nominal amount of initiator added. The solution is polymerized and crosslinked either by ultraviolet (UV) radiation (e.g., 254 nm for at least about 15 minutes, or other appropriate UV conditions, collectively termed "photopolymerization"), or by thermal initiation at elevated temperature (e.g., typically at about 40° C.). Following polymerization and crosslinking, the top glass slide is removed from the surface to uncover the gel. The pore size (and hence the "sieving properties") of the gel is controlled by changing the amount of crosslinker and the percent solids in the monomer solution. The pore size also can be controlled by changing the polymerization temperature.

In the fabrication of polyacrylamide hydrogel arrays (i.e., patterned gels) used as binding layers for biological molecules, the acrylamide solution typically is imaged through a mask during the UV polymerization/crosslinking step. The top glass slide is removed after polymerization, and the unpolymerized monomer is washed away (developed) with water, leaving a fine feature pattern of polyacrylamide hydrogel, which is used to produce the crosslinked polyacrylamide hydrogel pads. Further, in an application of lithographic techniques known in the semiconductor industry, light can be applied to discrete locations on the surface of a polyacrylamide hydrogel to activate these specified regions for the attachment of an oligonucleotide, an antibody, an antigen, a hormone, hormone receptor, a ligand or a polysaccharide on the surface (e.g., a polyacrylamide hydrogel surface) of a solid support (see, for example, International Application, Publication No. WO 91/07087, incorporated by reference).

For hydrogel-based arrays using polyacrylamide, biomolecules (such as oligonucleotides) are covalently attached by forming an amide, ester or disulfide bond between the biomolecule and a derivatized polymer comprising the cognate chemical group. Covalent attachment of the biomolecule to the polymer is usually performed after polymerization and chemical cross-linking of the polymer is completed Alternatively, oligonucleotides bearing 5'-terminal acrylamide modifications can be used that efficiently copolymerize with acrylamide monomers to form DNA-containing polyacrylamide copolymers (Rehman et al., 1999, *Nucleic Acids Research* 27: 649–655). Using this approach, stable probe-containing layers can be fabricated on supports (e.g., microtiter plates and silanized glass) having exposed acrylic groups. This approach has made available the commercially marketed "Acrydite™" capture probes (available from Mosaic Technologies, Boston, Mass.). The Acrydite moiety is a phosporamidite that contains an ethylene group capable of free-radical copolymerization with acrylamide, and which can be used in standard DNA synthesizers to introduce copolymerizable groups at the 5' terminus of any oligonucleotide probe.

With reference to the illustration provided in FIG. 1, the invention provides a hybridization chamber 10 comprising a biochip, which comprises a substrate 11 having a first surface 12 and a second surface 13 opposite thereto, and a flexible layer 16 affixed to the first substrate surface 12 by an adhesive layer 15. On the first surface 12 is an area 14 bounded by adhesive layer 15 an completely covered by flexible layer 16. Flexible layer 16, adhesive layer 15, and first substrate surface 12 further define a volume 25. The ratio of volume 25 to area 14 is preferably from about 0.025 $\mu$L/mm$^2$ to about 0.25 $\mu$L/mm$^2$, more preferably from about 0.1 $\mu$L/mm$^2$ to about 0.25 $\mu$L/mm$^2$, and most preferably from about 0.1 $\mu$L/mm$^2$ to about 0.2 $\mu$L/mm$^2$.

As shown in FIG. 3, between flexible layer 16 and first substrate surface 12 in area 14 is positioned an array 17 of biomolecules, which is preferably affixed to first substrate surface 12. Array 17 most preferably further comprises gel pads 22. FIG. 2 provides an exploded cross-sectional view of a portion of array 17 illustrating the gel pads 22. Each gel structure 22 is preferably cylindrical, most preferably having about a 113 micron diameter and about a 25 micron thickness. The distance between each site within each array 17 is most preferably about 300 microns.

A layer of a water-soluble compound 28 having a melting point of about 30 to about 60° C., more preferably of about 35 to about 50° C., and most preferably of about 35 to about 45° C. is deposited in volume 25 bounded by first substrate surface 12, flexible layer 16, and adhesive layer 15. Preferably, the water-soluble compound is biocompatible, does not stick to flexible layer 16, and serves to prevent mechanical damage to gel pads 22. In a preferred embodiment, the compound is polyethylene glycol, most preferably polyethylene glycol 600. The compound 28 is deposited so that the entire volume 25, with the exception of that portion of volume 25 occupied by array 17, comprises compound 28.

Array 17 can be positioned on surface 12 by providing markings, most preferably holes or pits in surface 12, that act as fiducials or reference points on surface 12 for accurate placement of array 17. The presence of said fiducials is particularly advantageous in embodiments comprising a multiplicity of arrays 17 in one or a multiplicity of areas 14 on surface 12, wherein accurate placement of said arrays is required for proper spacing and orientation of the arrays on the hybridization chamber.

Substrate 11 further comprises a first port 19 that transverses the substrate from the first surface 12 to the second surface 13 and forms first and second openings 29 and 30 on said first and second surfaces, respectively. The first port 19 serves as an input port and is positioned in substrate 11 so that the first opening 29 is provided within the area 14 bounded by adhesive layer 15 on first surface 12. In further preferred embodiments, substrate 11 further comprises a second port 20 that transverses the substrate from first surface 12 to second surface 13 and forms first and second openings 31 and 32 on said first and second surfaces, respectively. Second port 20 serves as an outlet port and is positioned in substrate 11 so that the first opening 31 opens within area 14 bounded by the adhesive layer 15 on the first surface 12. The second openings of ports 19 and 20 are covered with a removable and replaceable cover 21. In preferred embodiments, replaceable cover 21 is a stopper, a gasket, or tape, most preferably foil tape.

Input and output ports 19 and 20 are preferably shaped to accept a plastic pipette tip, most preferably a 10 $\mu$L pipette tip or a 200 $\mu$L pipette tip. In preferred embodiments, input and output ports 19 and 20 are generally in the shape of a truncated cone, as shown in FIG. 4, wherein the end of the cone having the smallest diameter forms the first opening of each port, 29 and 31 respectively, and the end of the cone having the largest diameter forms the second opening of each port, 30 and 32 respectively. This shape creates a seal between the pipette tip and the port, enhances visibility of the port for operator accuracy and prevents protrusion of the pipette tip into volume 25. In these embodiments, each port preferably has a diameter on the second surface of from about 1.0 mm to about 2.0 mm, and a diameter on the first surface of from about 0.3 mm to about 0.6 mm. The conical walls of ports 19 and 20 form an angle 54 with the second substrate surface 13, which is preferably less than 90°. Most preferably, angle 54 is less than or equal to the contact angle 55 of the solutions used for hybridization. Most preferably, angle 54 is equal to contact angle 55 such that the surface of the fluid in the port is flat. For aqueous solutions, this angle is about 60°. This geometric arrangement provides a port that tends not to leak and wicks fluid into volume 25 so that the second substrate surface 13 is dry when replaceable cover 21 is applied.

Substrate 11 is fabricated from any solid supporting substance, including but not limited to plastics, metals, ceramics, and glasses. Most preferably, substrate 11 is made from silicon or glass (for accuracy and stiffness), molded plastics (which reduce cost of manufacture and thermal inertia), or ceramics (for the incorporation of microfluidic elements including integrated heating elements). Most preferably, the substrate is glass.

Adhesive layer 15 is prepared using an adhesive suitable for forming a water-tight bond between substrate 11 and flexible layer 16, including, but not limited to, high temperature acrylics, rubber-based adhesives, and silicone-based adhesives. The shape of adhesive layer 15 is configured to contain array 17. Adhesive layer 15 can be deposited on first substrate surface 12 in a pattern to produce area 14 in any desired shape, and is most preferably deposited to define an ellipsoid area 14. Adhesive layer 15 can be deposited using inkjet printing or offset printing methods, or by die cutting the desired shapes from a sheet of adhesive material. In addition, a substantial portion of first surface 12 can be covered with adhesive and portions of the substrate which are not desired to retain adhesive properties can be hardened preferentially, for example, by ultraviolet curing. In these embodiments, portions retaining adhesive properties can be defined using a mask and thereby retain adhesive properties necessary to affix flexible layer 16 to surface 12. In embodiments using the die cut adhesive material, the adhesive material is preferably a double sided adhesive tape, and more preferably a double sided adhesive tape having no carrier. Adhesive layer 15 is most preferably set down in a layer between 1 and 100 $\mu$m thick, more preferably between 25 and 50 $\mu$m thick, and most preferably about 50 $\mu$m thick.

Flexible layer 16 is made of any flexible solid substance, including but not limited to plastics, including polypropylene, polyethylene, and polyvinylidene chloride (sold commercially as Saran® wrap) plastics, rubbers, including silicone rubbers, high temperature polyesters, and porous Teflon®. Flexible layer 16 is preferably biocompatible and preferably has low permeability in order to prevent evaporation of water from the volume contained between the flexible layer and the substrate. Flexible layer 16 also preferably is optically clear and should be able to withstand temperatures of between 50 and 95° C. for a period of between 8 and 12 hours without shrinkage. In a preferred embodiment, the flexible layer is a gas permeable membrane.

Flexible layer 16 preferably covers an area of from about 5 mm$^2$ to about 1400 mm$^2$, more preferably from about 5 mm$^2$ to about 600 mm$^2$, and most preferably from about 100 mm$^2$ to about 600 mm$^2$.

In preferred embodiments, as shown in FIG. 5, the invention further comprises a label layer 57 which is die cut in the same manner as the adhesive to form windows 58 that correspond in location to areas 14 on first substrate surface 12. The label layer is preferably a thick film having a layer of adhesive, and most preferably is an Avery laser label. The label layer is applied to the outer surface of the flexible layer, preferably by vacuum lamination.

Array 17 contained in area 14 on first substrate surface 12 is covered with a water-soluble compound 28, which protects and seals the biochip prior to use and prevents degradation or other damage to the array. Any water-soluble compound 28 having a melting point of about 30 to about 60° C., more preferably of about 35 to about 50° C., and most preferably of about 35 to about 45° C. is advantageously used in filling volume 25 between array 17 and flexible layer 16. Preferably, the compound is polyethylene glycol, most preferably polyethylene glycol 600. It is a particularly preferred feature of hybridization chamber 10 of the invention that water-soluble compound 28 fills the entirety of the volume 25 and more preferably also fills at least a portion of input port 19. This prevents formation of air bubbles in volume 25 because compound 28 is first melted, then carefully mixed with hybridization fluid 26 within volume 25 using a roller 40 without producing air bubbles in hybridization fluid 26. The lack of air bubbles in volume 25 minimizes artifactual signals detected by a scanner 36 or a light pipe 37.

Ports and holes can be produced in substrate 11 by diamond drilling in glass embodiments of substrate 11 or by stamping or molding in plastic embodiments thereof. This facilitates standardization of the hybridization chamber dimensions, for example, by producing substrates where the first and second ports 19 and 20 are produced in a single operation. Both the substrate 11 and the removable cover 21 can be set down as strips or large sheets, and can be rolled to avoid trapping air bubbles. Flexible layer 16 can be applied by vacuum lamination to avoid trapping air, or can be deposited by spinning or flowing liquid plastic over substrate 11 after treatment with adhesive 15 and water-soluble compound 28, followed by curing the flexible layer in place. Individual hybridization chambers 10 can be produced in stacks using, for example, a diamond saw as shown in FIG. 6.

FIG. 6 illustrates a preferred arrangement for manufacturing hybridization chamber 10, wherein alternating layers of flexible layer 16, adhesive layer 15, uncut substrate 11, and removable cover 21 are laid down, and hybridization chambers are produced by cutting the stacked layers, for example, with a diamond saw or any appropriate manufacturing tool. The sealed volumes 25 protect the arrays 17 from debris produced during the cutting process.

Alternative embodiments of the hybridization chamber 10 of the invention encompass a multiplicity of arrays 17 confined in a multiplicity of areas 14 underneath flexible layer 16, each area comprising an array 17 and being supplied with first port 19 and, optionally, second port 20. In these embodiments, adhesive layer 15 is deposited on first substrate surface 12 in a pattern that defines each of areas 14, and flexible layer 16 is applied to adhesive layer 15 to encompass areas 14 on said surface.

In certain embodiments of the invention, hybridization chamber 10 is produced containing array 17 or a multiplicity of arrays 17 as disclosed herein, wherein the chamber is provided ready-to-use by the addition of hybridization fluid 26 comprising one or a multiplicity of target molecules. In alternative embodiments, hybridization chamber 10 is provided without array 17, and allows for insertion thereof by a user. In these embodiments, at least one edge of flexible layer 16 is not adhered to first substrate surface 12.

In the use of the hybridization chamber 10 of the invention, an amount of a hybridization fluid 26, most preferably comprising a biological sample containing a target nucleic acid, is added to the hybridization chamber through first port 19. Before application of the hybridization fluid 26 to the chamber, volume 25 is most preferably heated to a temperature greater than or equal to the melting temperature of water-soluble compound 28. When melted, hybridization fluid 26 can be added to the chamber and mixed with the water-soluble compound, as shown in FIG. 1B. Preferably, water-soluble compound 28 does not affect hybridization in the chamber. More preferably, the amount of compound 28 is chosen such that hybridization efficiency is improved when compound 28 is mixed with sample fluid 26.

In embodiments of the chamber comprising first port 19 but not second port 20, the hybridization fluid is preferably introduced into the chamber after compound 28 is melted, and then the fluid is cycled into and out of the chamber using, most preferably, a pipette, until fluid 26 and compound 28 are fully mixed, and the hybridization fluid evenly distributed over the surface of array 17, or mixed into gel pads 22 comprising certain embodiments of said arrays. Alternatively, hybridization fluid 26 is evenly distributed over the surface of array 17, or mixed into gel pads 22 by physically manipulating flexible layer 16, as more fully described below. In these embodiments, hybridization fluid 26 is removed after hybridization is completed, as shown in FIG. 7, and array 17 is washed by the cycling a sufficient volume of a wash solution 27 into and out of the chamber, most preferably using a pipette.

In embodiments of the chamber comprising both first port 19 and second port 20, the hybridization fluid is preferably introduced into the chamber after compound 28 is melted, and then the fluid is cycled into and out of the chamber using, most preferably, at least one pipette, until fluid 26 and compound 28 are fully mixed, and the hybridization fluid evenly distributed over the surface of array 17, or mixed into gel pads 22 comprising certain embodiments of said biochips. Hybridization is then performed by incubating the chamber for a time and at a temperature sufficient for hybridization to be accomplished. Hybridization fluid 26 is removed after hybridization has been completed using outlet port 20, and the biochip washed by the addition and cycling of a sufficient volume of a wash solution 27 into and out of the chamber, most preferably using a pipette. In these embodiments, the wash solution can also be continuously provided by addition through the input port and removal through the output port. In certain embodiments, the biochip containing the hybridized array is removed from the chamber for development or further manipulations as required. In preferred embodiments, the biochip containing the hybridized array is analyzed in situ as described below.

FIG. 1B illustrates an advantageous embodiment of hybridization chamber 10 of the invention, further comprising a heating element 33. Most advantageously, heating element 33 has a heating surface 34 adapted to the shape of hybridization chamber 10 to substantially cover the area 14 under flexible layer 16. Heating element 33 is any suitable heating means, including but not limited to resistance heaters, thermoelectric heaters, or microwave absorbing heaters.

The hybridization chamber 10 of the invention also advantageously comprises a thermocouple 35 or other temperature-sensing or measuring element to measure the temperature of hybridization fluid 26 or chamber 10. These temperature-sensing elements advantageously are coupled with heating element 33 to control hybridization fluid 26 and wash solution 27 temperature, and can be used to calibrate other elements, such as scanning devices 36 as described below that may be sensitive to temperature.

In certain embodiments of the invention, positive hybridization is detected visually, i.e., by the production of a dye or other material that reflects visible light at sites on biochip 18 where hybridization has occurred. In these embodiments, the dye or other material is most preferably produced enzymatically, for example, using a hybridization-specific immunological reagent such as an antibody linked to an enzyme that catalyzes the production of the dye. Visual inspection can be used to detect sites of positive, hybridization. More preferably, the biochip containing the hybridized array is scanned using scanner 36 as disclosed more fully below.

Positive hybridization on biochip 18 most preferably is detected by fluorescence using labeled target molecules in a biological sample, or by including intercalating dyes in the hybridization fluid 26 that fluoresce when bound by a hybridized DNA duplex and illuminated by light at a particular wavelength. Suitable intercalating dyes include, but are not limited to, ethidium bromide, Hoechst DAPI, and Alexa Fluor dyes. Suitable fluorescence labels include, but are not limited to, fluorescein, rhodamine, propidium iodide, and Cy3 and Cy5 (Amersham), that can be incorporated into target molecules, for example, in vitro amplified fragments using labeled oligonucleotide primers.

FIGS. 8A–8C illustrate an embodiment of the invention comprising a scanner 36, which is advantageously positioned over (or beneath) flexible layer 16 and moves from one end of area 14 to the opposite end, sequentially illuminating area 14 and array 17 positioned thereupon. Prior to analysis of the hybridized array, all fluid is removed from volume 25 such that flexible layer 16 is in contact with array 17. Scanner 36 then excites the fluorescent dye, preferably with short wavelength light, most preferably light with a wavelength between 250 nm and 600 nm. Scanner 36 then collects the emitted light from a specific area. The amount of light emitted is then used to determine the amount of fluorescent dye present in the area, and hence the amount of labeled target.

Particular embodiments of scanners and scanning devices 36 are shown in FIGS. 9A through 9E. It is a particularly advantageous feature of hybridization chamber 10 that flexible layer 16 is translucent to suitable wavelengths of light, including light in the ultraviolet and visible portion of the spectrum. An additional advantageous feature of hybridization chamber 10 is that flexible layer 16, which is very thin, is immediately adjacent to and in contact with biochip 18 after hybridization fluid 26 or wash fluid 27 is removed from the chamber. This combination of features reduces or eliminates free surface reflections, internal reflection of illumination from the scanner, and dispersion or scattering of illuminating light, thereby optimizing the amount of incident light that illuminates array 17. This arrangement is also more economical than in existing apparatus as it minimizes the need for highly polished, low scattering surfaces or complex or expensive lenses, and eliminates problems associated with focus and depth-of-field in more complex optical detectors.

In other embodiments, a light pipe 37 contacts the surface of flexible layer 16 which is immediately adjacent to and in contact with the surface of array 17, as shown in FIG. 9B. In these embodiments, both illuminating and emitted light are conveyed and collected by light pipe 37. The pipe is designed to be slightly flexible so as to adapt to the contoured surface of flexible layer 16. Light pipe 37 contacts flexible layer 16 which contacts array 17, thereby permitting contacts free of surface reflections even under circumstances where array 17 or light pipe 37 has localized variations in height. Advantageously, light pipe 37 has a larger surface area than array 17, so that the maximum amount of illuminating light is delivered to array 17, and the maximum amount of emitted light from array 17 is collected by light pipe 37. A further advantage of light pipe 37 is that it enables detection of bubbles formed in hybridization fluid 26 or wash buffer 27, which detection can be used as a signal for roller 40 to address flexible layer 16 to remove such bubbles. Removing bubbles in hybridization fluid 26 or wash buffer 27 reduces the frequency of non-specific binding and artifactual signals detected by scanner 36.

In additional embodiments of the invention, the area 14 defined by adhesive layer 15 further comprises a reflective layer 38 that substantially covers the entirety of the area 14 and is positioned between array 17 and the first substrate surface 12. In preferred embodiments, reflective layer 38 comprises aluminum, gold, silver, or platinum. In these embodiments, the amount of the light signal reflected or transmitted to the light-detecting portion of scanner 36 is increased up to four-fold. In further advantageous embodiments of the invention, reflective layer 38 is a metal film resistor or an RF induction heater. In these embodiments, reflective 38 layer can heat the slide without requiring additional heating elements 33. This is a particularly desirable feature in hand-held embodiments of the hybridization chamber 10 of the invention.

If required, a passivation later 39 can be applied on top of reflective layer 38. Preferably, passivation layer 39 is a layer of parylene a few microns thick that is applied by evaporation. The amount of illumination required, and hence the amount of power needed to operate scanner 36 is reduced in these embodiments, which are particularly suited to battery-operated embodiments such as hand-held devices to improve useful battery life. Furthermore, passivation layer 39 reduces artifactual signals in the light emission data by obscuring objects that it covers.

Hybridization chamber 10 is preferably supplied with a roller 40 in removable contact with flexible layer 16 and that can be moved longitudinally across areas 14 on first substrate surface 12. In preferred embodiments, the surface of roller 40 comprises a textured pattern 41, most preferably a spiral pattern, that permits the roller to efficiently mix hybridization fluid and wash solution across area 14 and array 17. One advantageous arrangement of roller 40 and hybridization chamber 10 is shown in FIG. 9E. As shown in the Figure, roller 40 can be advantageously connected to a movable arm 42 that can be positioned to place roller 40 in contact with flexible layer 16 when in a first position, and can be moved to a second position in which roller 40 is not in contact with flexible layer 16. Most preferably, movable arm 42 has a pivot point 44 and movement about said pivot point is preferably controlled by a solenoid. In addition to movement of roller 40 in contact with and away from hybridization chamber 10, either roller 40 or hybridization chamber 10, or both, are movable in a longitudinal direction to enable roller 40 to mix hybridization fluid 26 or wash solution 27 inside volume 25 bounded by flexible layer 16, adhesive layer 15, and first substrate surface 12 in area 14 containing array 17. In embodiments comprising a multiplicity of areas 14 containing a multiplicity of arrays 17, roller 40 is positioned to move longitudinally across each of the multiplicity of areas 14 to mix hybridization fluid 26 or wash solution 27 in each of the volumes 25 containing arrays 17.

In additional embodiments, a sample preparation chip 45, comprising a port 46, as shown in FIGS. 10A through 10C, can be attached to hybridization chamber 10. Most preferably, port 46 in sample preparation chip 45 is aligned with first port 19 in hybridization chamber 10 to permit efficient transfer of sample to volume 25. Additional fiducial references can be used to accurately align hybridization chamber 10 and sample preparation chip 45. Since access to first port 19 is through second substrate surface 13, the array can be scanned without interference from the attached sample preparation chip. In alternative embodiments of the invention, sample preparation chip 45 may be bound to second substrate surface 13 (FIG. 10B) or formed as an integral part of substrate 11 (FIG. 10C).

A preferred embodiment of hybridization chamber 10 of the invention is a hand-held embodiment as shown in FIGS. 8A–8C, further comprising a scanner 36. In these embodiments, hand-held device 47 comprises a base 48, a lid 49 and a carriage 50 embodying roller 40, scanner 36, heating element 33 and thermocouple 35. Carriage 50 is illustrated in FIG. 9A. Device 47 comprises a compartment 51 for positioning hybridization chamber 10 in proximity to carriage 50. Carriage 50 is provided with moving means for moving roller 40, scanner 36 and heating element 33 relative to hybridization chamber 10 as required for operation as described above. Carriage 50 and lid 49 are arranged to permit a user to introduce and remove hybridization fluid 26 and wash solution 27 into the chamber through first port 19 and second port 20 as required. Alternatively, device 47 further comprises fluidic connections 52 to each of the first and second ports to provide for sample introduction and array washing after hybridization of the sample thereto. Device 47 is most preferably operated by battery, although AC adapters are also advantageously encompassed by the description of the device herein. In further preferred embodiments, lid 49 further comprises a display 56 for displaying the results of the analysis.

The Examples that follow are illustrative of specific embodiments of the invention and various uses thereof. They are set forth for explanatory purposes only, and are not to be taken as limiting the invention.

EXAMPLE 1

ASSEMBLY OF A HYBRIDIZATION CHAMBER

The process of assembling a chamber according to the present invention is illustrated in FIG. 11.

A die cutter was used to cut four ellipsoidal holes in a layer of 502FL ultra-clean laminating adhesive film (3M). A similar pattern was punched into an Avery laser label 5663 for use as a frame and label layer. Meanwhile, a sheet of polyvinylidene chloride film was stretched over a stainless steel frame and annealed for 30 minutes at 100° C. The Avery label was applied to one side of the polyvinylidine chloride film by vacuum laminating the label in a vacuum lamination press. A vacuum of 15 psi was applied for 30 seconds, and mechanical pressure of 15 psi was maintained for 1 minute after release of the vacuum. The adhesive was then applied to the opposite side of the polyvinylidene chloride film using the same process as for the label.

The adhesive coated film was then applied to a glass slide which had previously been prepared. The arrays of oligo-nucleotide probes and gel pads were positioned on the glass slide using standard methods. Ports were drilled into the slide using a diamond drill. A vacuum lamination press was used to affix the polyvinylidene chloride film to the slide. A vacuum of 15 psi was maintained for 1 minute, and then mechanical pressure of 15 psi was maintained for an additional minute.

The individual chambers were then filled with polyethylene glycol 600 using a 10 µl pipette tip. A layer of 3M 7350 polyester tape was then applied to the slide to seal off the ports.

It should be understood that the foregoing disclosure emphasizes certain specific embodiments of the invention and that all modifications or alternatives equivalent thereto are within the spirit and scope of the invention as set forth in the appended claims.

What we claim is:

1. An apparatus for performing biological reactions, comprising:
    (a) a glass microscope slide having a first surface and a second surface opposite thereto;
    (b) an array of biomolecules positioned on the first surface of the slide, wherein each biomolecule within the array is anchored to the first surface by a polyacrylamide gel pad;
    (c) a layer of polyvinylidene chloride affixed to the first surface of the slide by a layer of double-sided adhesive, wherein the adhesive layer is deposited on the first surface of the slide and encloses an area thereupon;
    (d) a first and second port extending through the slide from the first surface to the second surface thereof each having a first opening and a second opening, wherein the first opening of each port is provided within the area on the first surface of the slide bounded by the adhesive and covered by the flexible layer and the second opening of each port is provided on the second surface of the slide, and wherein each port is in the shape of a truncated cone having a small-diameter end and a large diameter end, and wherein the small diameter end is the first opening and the large diameter end is the second opening;
    (e) a layer of foil tape positioned over the second opening of each port;
    (f) a layer of a polyethylene glycol positioned between the first surface of the slide and the layer of polyvinylidene chloride;
    (g) a reflective layer positioned between the array and the first substrate surface;
    (h) a layer of parylene positioned between the reflective layer and the layer of polyvinylidene chloride; and
    (i) a resistive heater.

2. An apparatus for performing biological reactions, comprising:
    (a) a glass microscope slide having a first surface and a second surface opposite thereto,
    (b) an array of biomolecules positioned on the first surface of the slide, wherein each biomolecule within the array is anchored to the first surface by a polyacrylamide gel pad;
    (c) a layer of polyvinylidene chloride affixed to the first surface of the slide by a layer of double-sided adhesive, wherein the adhesive layer is deposited on the first surface of the slide and encloses an area thereupon;
    (d) a first and second port extending through the slide from the first surface to the second surface thereof each having a first opening and a second opening, wherein the first opening of each port is provided within the area on the first surface of the slide bounded by the adhesive and covered by the flexible layer and the second opening of each port is provided on the second surface of the slide, and wherein each port is in the shape of a truncated cone having a small-diameter end and a large diameter end, and wherein the small diameter end is the first opening and the large diameter end is the second opening;
    (e) a layer of foil tape positioned over the second opening of each port;
    (f) a layer of a polyethylene glycol positioned between the first surface of the slide and the layer of polyvinylidene chloride;
    (g) a reflective layer positioned between the array and the first substrate surface;
    (h) a layer of parylene positioned between the reflective layer and the layer of polyvinylidene chloride;
    (i) a resistive heater;
    a case having a lid and a base, wherein the lid further comprises a display unit;
    (k) a cavity disposed in the base; and
    (l) a carriage comprising a scanner and a roller, wherein the carriage is provided in the cavity, and wherein the slide is removably positioned above the carriage such that the first slide surface is in operative contact with the carriage.

3. An apparatus for performing biological reactions comprising:
   a) a substrate comprising a first and a second surface;
   b) an array of biomolecular probes positioned on said first surface;
   c) a flexible layer comprising a gas permeable membrane affixed to said first surface by an adhesive layer, forming a reaction volume; and
   d) a port extending through said substrate from said second surface to said first surface.

4. An apparatus for performing biological reactions comprising:
   a) a substrate comprising a first and a second surface;
   b) an array of biomolecular probes positioned on said first surface;
   c) a flexible layer affixed to said first surface by an adhesive layer, forming a reaction volume;
   d) a port extending through said substrate from said second surface to said first surface;
   e) a sample preparation chip; and
   wherein said port is a first port that extends from said second surface to said reaction volume and said sample preparation chip is in contact with said second surface and wherein said sample preparation chip has a port that is aligned with said first port.

5. An apparatus for performing biological reactions comprising:
   a) a substrate comprising a first and a second surface;
   b) an array of biomolecular probes positioned on said first surface;
   c) a flexible layer affixed to said first surface by an adhesive layer, forming a reaction volume; and
   d) a port extending through said substrate from said second surface to said first surface; and
   e) a roller, wherein said roller is in contact with said flexible layer.

6. A method of making an apparatus comprising:
   a) providing a substrate with a first and a second surface, wherein said first surface comprises a continuous layer of derivatized polyacrylamide;
   b) contacting said derivatized polyacrylamide with biomolecular probes;
   c) forming an amide bond between said derivatized polyacrylamide and said biomolecular probe;
   d) adding a flexible layer comprising a gas permeable membrane to said first surface to form a reaction volume.

7. A method of detecting the presence of a target molecule in a sample comprising:
   a) providing an apparatus comprising:
      i) a substrate comprising a first and a second surface;
      ii) an array of biomolecular probes positioned on said first surface; and
      iii) a flexible layer comprising a gas permeable membrane affixed to said first surface by an adhesive layer, forming a reaction volume;
      wherein said apparatus comprises at least a first port into said reaction volume;
   b) introducing said sample through said first port into said reaction volume under conditions that allow the binding of said target molecule to at least one of said biomolecular probes; and
   c) detecting said binding as an indication of the presence of said target molecule.

8. An apparatus according to claim 3, 4, or 5 wherein said biomolecular probes are oligonucleotides.

9. An apparatus according to claim 3, 4, or 5 wherein said biomolecular probes are DNA.

10. An apparatus according to claim 3, 4, or 5 wherein said substrate comprises glass.

11. An apparatus according to claim 3, 4, or 5 wherein said substrate comprises a polymer.

12. An apparatus according to claim 3, 4, or 5 wherein said substrate comprises ceramic.

13. An apparatus according to claim 3, 4, or 5 wherein said substrate comprises silicon.

14. An apparatus according to claim 3, 4, or 5 wherein said biomolecular probes are anchored to said first surface using polyacrylamide.

15. An apparatus according to claim 3, 4, or 5 further comprising a heating element positioned under said reaction volume.

16. An apparatus according to claim 15 wherein said heating element is a resistive heater.

17. An apparatus according to claim 3, 4, or 5 comprising a plurality of arrays of said biomolecular probes; and said flexible layer, said adhesive layer and said first surface comprise a plurality of reaction volumes each containing one of said arrays.

18. An apparatus according to claim 3, 4, or 5 wherein said reaction volume further comprises a water-soluble compound that is a solid at room temperature and a liquid at a second, higher temperature.

19. An apparatus according to claim 3, 4, or 5 further comprising a scanner.

20. An apparatus according to claim 3 or 5 further comprising a sample preparation chip.

21. A method according to claim 7 wherein said target molecule is labeled with a fluorescent label.

22. A method according to claim 7 wherein said biomolecular probes are nucleic acids.

23. A method according to claim 7 wherein said target molecule is a nucleic acid.

* * * * *